United States Patent [19]
Fachinger et al.

[11] Patent Number: 5,528,363
[45] Date of Patent: Jun. 18, 1996

[54] INTEGRATED DEVICE FOR INSTANTANEOUS DETECTION AND IDENTIFICATION OF AN ENTITY

[75] Inventors: Claude Fachinger, Chambery; Michel Martin-Bouyer, Barberaz; Emmanuel Naffrechoux, Saint Alban Leysse; Joël Suptil, Chambery, all of France

[73] Assignee: Universite de Savoie, France

[21] Appl. No.: 360,744

[22] PCT Filed: Apr. 27, 1994

[86] PCT No.: PCT/FR94/00478

§ 371 Date: Dec. 22, 1994

§ 102(e) Date: Dec. 22, 1994

[87] PCT Pub. No.: WO94/25837

PCT Pub. Date: Nov. 10, 1994

[30] Foreign Application Priority Data

Apr. 27, 1993 [FR] France .................. 93 05204

[51] Int. Cl.⁶ .................. G01J 3/18; G01J 3/28
[52] U.S. Cl. .................. 356/326; 356/328
[58] Field of Search .................. 356/326, 328, 356/301; 364/498; 250/551, 214 AL

[56] References Cited

U.S. PATENT DOCUMENTS

| | | | |
|---|---|---|---|
| 3,846,024 | 11/1974 | Turner | 356/329 |
| 4,560,275 | 12/1985 | Goetz | 356/326 |
| 5,139,334 | 8/1992 | Clarke | 356/301 |

FOREIGN PATENT DOCUMENTS

| | | |
|---|---|---|
| 0319769 | 6/1989 | European Pat. Off. . |
| 0368560 | 5/1990 | European Pat. Off. . |
| 0315939 | 8/1990 | European Pat. Off. . |
| 0399057 | 11/1990 | European Pat. Off. . |
| 0520322 | 12/1992 | European Pat. Off. . |
| 2078368 | 1/1982 | United Kingdom . |
| 2217006 | 10/1989 | United Kingdom . |
| 9013810 | 11/1990 | WIPO . |

OTHER PUBLICATIONS

Measures Regulation Automatisme, vol. 51, No. 15, (Nov. 1986), Paris France pp. 47–63.
Analytical Chemistry, vol. 62, No. 11, (1989), pp. 1249–1252.
Review of Scientific Instruments, vol. 57, No. 12, (Dec. 1986) pp. 2995–3003.
Zeiss Information, vol. 30, No. 100, (Apr. 1990), pp. 16–19.
Electronic Design, vol. 38, No. 23, (Dec. 1990), pp. 32–34.
Advances in Instrumentation and Control, vol. 46, No. 1, (1991), pp. 333–340.

*Primary Examiner*—F. L. Evans
*Attorney, Agent, or Firm*—Harris Beach & Wilcox

[57] ABSTRACT

This integrated device for instantaneously carrying out qualitative and quantitative identification of one or more physicochemical entities contained in or on a sample and capable of producing one or more emission or absorption or reflection spectra under excitation by an electromagnetic wave comprises, within a shielded casing (1):

a polychromator (5) to which the emission, absorption or reflection spectrum or spectra of the analyzed sample is or are conveyed, an element (6) for detecting said signals, which is positioned on the optical path of the signals output by the polychromator (5), a conversion circuit (6), coupled with said polychromator (5), a central processing unit (7) incorporating, in an associated memory, a plurality of standard spectra representative of known and predetermined entities and intended to analyze the digital spectrum or spectra thus obtained and to compare, after decorrelation, this spectrum or these spectra with the spectra stored in said memory, and to deduce from this comparison the nature and the concentration of the predetermined physicochemical entity or entities in or on the sample.

3 Claims, 1 Drawing Sheet

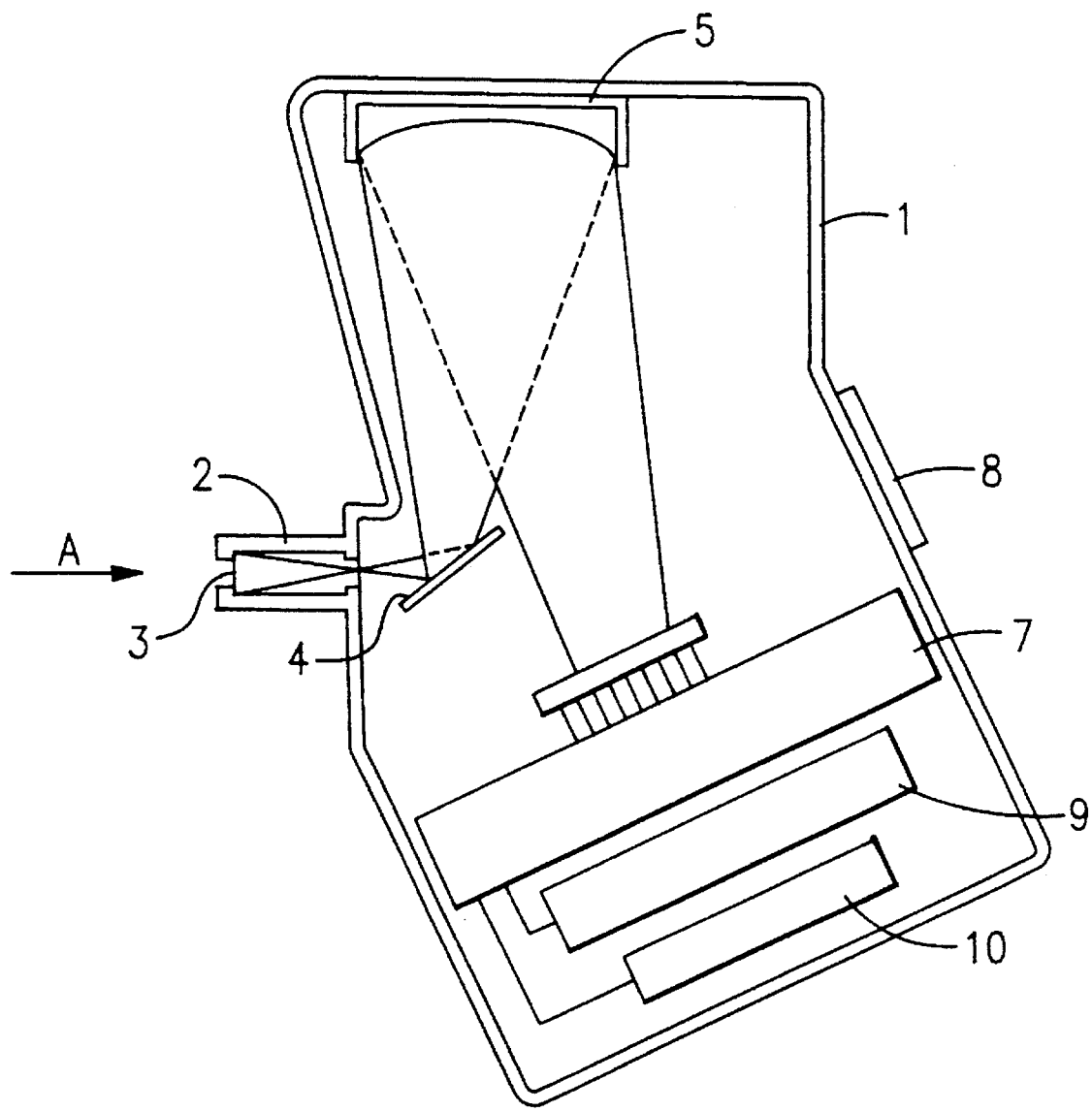

INTEGRATED DEVICE FOR INSTANTANEOUS DETECTION AND IDENTIFICATION OF AN ENTITY

BACKGROUND OF THE INVENTION

The invention relates to an integrated and compact device making it possible to carry out qualitative and quantitative identification of one or of a plurality of physicochemical entities contained in a fluid, and to do this instantaneously.

It is increasingly being sought to be able to carry out instantaneous analysis of fluid, liquid or gas samples, that is to say without prior physical or chemical treatment, and without addition of any reagent. The advantage of providing such a possibility can be seen, in particular, in the fields of pollution, toxicology, or, in short, in the field of environmental science, and in general in any field in which the identification of any entity induces the triggering of a certain number of processes. Now, there is currently no device available which can carry out this analysis instantaneously and is capable of being operational for a range of entities which is wide enough to be truly useful.

At the very best there is available a technique employing a device which exploits one or two different wavelengths in the absorption spectrum for measuring the concentration of certain chemical species (see, for example, EP-A-0,399,057). They lead to unsatisfactory results insofar as the number of entities detectable is small, and the concentrations measured are relatively approximate. In parallel, the equipment employed for achieving these measurements is heavy and complex, preventing any on-site measurement.

More conventionally, the devices available consist of measurement chains or acquisition stations, in which each of the parts has its own function, namely detector, monochromator, processing unit. In addition, they all require prior treatment of the liquid or fluid to be analyzed, such as, in particular, separation, in which each of the phases is analyzed independently of the others, allowing, after processing and analysis, reconstruction in terms of quality and concentration of the basic fluid or of the raw fluid.

SUMMARY OF THE INVENTION

The object of the invention is to provide a device which is capable of processing, on-line and instantaneously, data output by multiwavelength detectors, and in particular to provide, in addition to qualitative indications, also the concentration of certain predetermined chemical species, and to do this directly from a raw medium, that is to say one having no prior physical or chemical treatment, and thereby to estimate the quality of a sample by comparing the data thus collected with those contained in a database, so as to constitute a compact and integrated expert system which can be used on site.

This integrated device for instantaneously carrying out qualitative and quantitative identification of one or of a plurality of physicochemical entities contained in or on a sample and capable of producing one or more emission, absorption or reflection spectra under excitation by an electromagnetic wave, is characterized in that it comprises, within a shielded casing:

a polychromator to which the emission, absorption or reflection spectrum or spectra of the analyzed sample is conveyed and which is intended, in a known manner, to decompose this spectrum or these spectra into a sequence of optical signals having discrete variation in wavelength, an element for detecting optical signals, positioned on the optical path of the signals output by the polychromator and intended to convert said optical signals into analog signals, a conversion circuit, coupled with said detection element and intended to convert said analog signals into digital signals, a central unit, incorporating, in an associated memory, a plurality of standard spectra representative of known and predetermined entities, and intended simultaneously to analyze the digital spectra thus obtained and to compare, after decorrelation, these spectra with the spectra stored in said memory, and to deduce from this comparison the nature and the concentration of the predetermined physicochemical entity or entities in the sample.

In other words, the invention consists in using as data source the emission, absorption or reflection spectra of the medium or of a sample of the medium analyzed, and in decorrelating these spectra with a view to determining the species present which are responsible for the colour. This spectral analysis is carried out instantaneously and independently of any prior treatment as regards the medium studied, so that it is possible to provide a very fast response and thereby to use this device for any type of expert system. In addition, since all the constituents of this casing are integrated within a shielded casing, the analyzes carried out are free of any interference inherent with both magnetic fields, electric fields and external pressure variations.

In other words, the invention consists in integrating, within one and the same apparatus, which is moreover of compact shape, various elements capable of completely analyzing an absorption or emission spectrum and of determining the nature and the respective quantity of a certain number of predetermined entities contained in the analyzed sample.

In a particular embodiment of the invention, the result of this analysis, obtained directly in plain form, causes the central unit to induce automatic triggering of sensor signals or the activation of defined elements, motors, robots, etc. In this way, by virtue of this device, it is possible to obtain immediate on-line analysis and thereby to induce, as a function of this analysis, the activation of any associated element, in the context of safety measures, warnings, etc.

Advantageously, the circuit for detecting the optical signals output by the polychromator consists of a linear array of photodiodes or of a charge-coupled circuit (CCD type circuit), or of any other detector capable of delivering an analog or digital signal referring to a wavelength.

In addition, the acquisition of the emission, absorption or reflection spectrum of the analyzed sample consists, if this sample is liquid, of an assay cell having at least two parallel quartz walls which are transparent to the electromagnetic excitation beam, it being possible for these walls optionally to be virtual and fed by fibre-optic devices, for example.

In the context of acquisition of a spectrum of a gas sample, the cell is replaced by a multiple-reflection cell which is also transparent to the excitation beam.

According to an advantageous characteristic of the invention, the device also includes an integrated electrical supply generator, consisting, for example, of a plurality of photoelectric cells positioned outside the casing, so as to make this device autonomous, thus favouring its use on site.

The manner in which the invention may be embodied and the advantages which result therefrom will emerge better from the exemplary embodiments which follow, given by way of indication and without any implied limitation, supported by the single attached figure which corresponds to a diagrammatic representation of the device according to the invention.

BRIEF DESCRIPTION OF THE DRAWINGS

The device according to the invention and diagrammatically represented in FIG. 1 essentially includes an enclosure or casing (1), having an opening to which the emission or absorption spectrum emitted by a liquid or gas sample is conveyed by means of a collimator (2) and an objective lens (3). This casing is shielded, so that the internal volume which it defines is insensitive both to magnetic and electric fields and to external pressure variations. In addition, it is also light-tight, with the exception of the opening which it has, and also liquid-tight. In this way, this device can perfectly well be used in a hostile atmosphere, in particular industrial or natural, which was not possible with devices hitherto known.

DETAILED DESCRIPTION OF THE INVENTION

This spectrum is conveyed by any known means, and in particular by means of an optical fibre or a plurality of optical fibres. The arrow A represents the arrival of this spectrum at the objective lens (3) of the collimator (2).

The electromagnetic wave carrying this spectrum is then reflected by a mirror (4) onto a polychromator (5) consisting, for example, of a flat-field grating intended to diffract the electromagnetic waves incident on it into a plurality of monochromatic beams having a wavelength which is a function of the diffraction angle. These various beams reach a linear array of 512 photodiodes (6) intended to convert the electromagnetic signal received into an analog signal, which is representative of the luminous intensity of said electromagnetic signal. In this way, the linear array of photodiodes (6) or any other equivalent device produces an analog spectrum from the spectrum decomposed by the polychromator into a discrete sequence of wavelengths.

In order to be capable, during the subsequent step, of undergoing digital processing, in particular in a central processing unit, the analog signals output by the sensors are converted into digital signals by means of an analog/digital converter integrated with said sensor, and for example connected thereon. In this way, such a convertor may be in the form of an electronics board of particularly small bulk. In another embodiment of the invention, the linear array is replaced by a charge-coupled device (CCD) which, in a known manner, directly converts the electromagnetic signals into digital signals. By virtue of the use of such a CCD, it is then possible simultaneously to record a plurality of spectra, so as to make it possible to determine, using optical fibres, the colour or the volume of a sample. In conjunction, it then becomes possible instantaneously to measure the temperature at different points of a sample.

The digital signals thus obtained are then processed in a central processing unit (7), typically consisting of a plurality of electronics boards, still with the same aim of achieving optimum compactness of the device. This unit, integrated in the enclosure (1) of the device, includes an associated memory in which a plurality of spectra representative of predetermined physical or chemical entities is stored.

In addition, suitable software is loaded in this processing unit (7) and is intended to compare the spectrum output by the charge-coupled circuit or the linear array of photodiodes with the various spectra stored in the associated memory. In order to do this, the absorbance measured for a defined wavelength is considered as being equal to the sum of the absorbances of the various chemical entities present in the sample, supplemented by a contribution from the spectral background coming from interference.

Suitable digital processing carried out in said processing unit (7) compares the absorbance values measured for said defined wavelength with that of a file contained in the associated memory, incorporating the absorbance values of the constituents to be assayed.

This calculation leads to a precise value of the concentration of the desired constituent. Consistency between measurement and model is ensured by the use of multimodel systems, which are known per se, which adjust the measured and calculated absorbance values.

In parallel, by virtue of the connection method used, namely direct connection, both for the analog/digital converter onto the detector element (6) and for the boards constituting the microcontroller (7) onto said converter element, it is thus possible to accelerate the analysis speed and to overcome possible signal distortions inherent with the background noise and which have a parasitic effect on the measurements.

In addition, in order to optimize the compactness of the device, it is possible to make it autonomous as regards power supply by adding to it photoelectric cells (8) located on one of the faces of the enclosure (1) and intended, in a known manner, to convert the light energy into electrical energy.

In addition, in order to make it possible immediately to provide the result of the analysis or analyses carried out on the site itself, it is possible to add to the device a screen (9), for example a liquidcrystal screen, as well as a mini-keyboard (10), both being connected to the microcomputer (7), the said keyboard allowing optional input of parameters into said microcomputer (7), on the basis of external conditions or of the analyzed medium.

Depending on the phase of the analyzed sample, use is made either of an assay cell having at least two parallel-quartz faces, which are therefore transparent to the excitation beam, of the type described in document FR-A-2,674,959, or of a multiple-reflection cell in the case of a gas, which cell comprises, in a known manner, a resonant chamber in which said gas is subjected to an incident excitation beam, typically consisting of ultraviolet or laser radiation which can pass through said chamber and induce the emergence of radiation corresponding to the absorption and emission spectrum of the gas or of the air contained in said chamber.

In a particular application of the invention, in situ analysis can be carried out by means of a highly collimated laser beam, this being in the context of pollution monitoring of ambient air, in particular in an industrial or urban environment.

A first application of this device consists in carrying out instantaneous assaying of defined chemical species, such as, in particular, nitrates, phenol, hexavalent chromium, metals—such as iron, copper, manganese, lead, zinc, cadmium—organic products, chlorides, borates, phosphates, ammonium, etc., this being in a liquid sample.

This application lies within the context of research and determination of global pollution parameters and also of toxicity analysis of liquid media, especially measurement of the suitability of water for drinking. In fact, in addition to research on entities of the type of those previously mentioned, values of Total Organic Carbon, or other concepts, such as Chemical Oxygen Demand, which is well known in the field of pollution, of oxidizable materials and, under certain conditions, of Biological Oxygen Demand are measured on samples of untreated water.

On the basis of this information, the device according to the invention provides a biological quality index, the result of which is obtained directly, either in plain form on the screen (9) associated with said central unit, or in the form of digital or analog signals which can activate a triggering of other sensor, light or audible signals, for example, or else the activation of particular elements. In the latter case, automatic control of industrial processes, in which the preceding device is integrated in the circuits controlling the manufacture of various products, especially chemical products, is associated with the device.

These optical measurements may additionally be supplemented by the addition by the user, or collection by the internal computer, of external data, such as, in particular, those coming from sensors for measuring flow rate and physical or physicochemical data such as pH, rH (Redox potential), temperature, conductivity, dissolved oxygen quantity, turbidity, in order to constitute an automatic "toximeter", that is to say a device which can automatically and instantaneously measure the toxicity of a given medium and, in particular, of water.

Of course, the device of the invention can be coupled with a monitoring network made from a series of sensors which transmit the data collected on the monitoring sites via telephone, radio waves or else by satellite, so as to make it possible continuously to monitor the quality of industrial production, or the quality of natural water in a catchment area, or else the degree of pollution of the air on an industrial site or an urbanized area.

By adding a physicochemical measurement chain to the preceding integrated station, a new apparatus is achieved in which it is possible, by inputting a spectrum database referring to identical scenarios of accidental pollution, to classify the water in real time as a function of its degree of quality or toxicity, in view of the analysis carried out instantaneously, without requiring prior physicochemical treatment such as settling.

This application can also be assigned to the determination of the quality of ambient air, in particular in industrial premises.

In other words, a warning station is produced which can activate any triggering of audible or visual alarm when a certain threshold is exceeded or can induce the activation of motor elements in the particular case of closure of valves, shutdown of pumps for the drinking water supply network, or the implementation of preestablished alarm programs.

In the same way, coupled with a control device for the atmospheric air supply of a biological treatment tank, it is possible, by determining the returning COD and the physicochemical parameters, integrally to control a wastewater treatment station and thereby substantially to reduce the operating and maintenance costs of such an installation. It is also possible to provide the device with the capacity of determining the biodegradability of water and thereby to predict operation of said station.

In a quite different application, it is known that the color of the flame of a plasma torch varies as a function of the metals which it encounters. By virtue of this, and by analyzing this color using the device of the invention, it is possible to control the machining installation in real time. In fact, in a known manner, the observed color depends directly on the wavelengths of the corresponding absorption or emission spectrum. In this field, the device can instantaneously analyze the plasma emission spectrum.

In addition to these various applications, the device of the invention can also be used in time [sic] as laboratory spectrophotometer, in particular in the context of high-pressure liquid-phase chromatography analyses, but also during reaction kinetics measurements, in RAMAN and infrared spectroscopy and for temperature measurements of flames or of solids.

According to an advantageous characteristic of the invention, this device can be used for optical detection and identification of an entity and, in particular, in the context of identification and recognition of articles. These articles are advantageously provided with an identifier, consisting, for example, of a pellet having an area of a few square millimeters, having any shape, but having a specific color defined by its wavelength. This actually has a characteristic and unique absorption and emission spectrum, by virtue of the uniqueness of the multiwavelength spectrum corresponding to the associated color. A color code can then be printed and constitutes an identifier.

In other particular applications, application of a pellet onto the identified object can be avoided, with the identifier consisting of the object or the entity itself, insofar as the absorption or emission spectrum linked with its color has been produced and classified beforehand. Typically, this pellet can be adhesively bonded or fixed by any suitable means onto the object to be recognized.

Nevertheless, it can be printed when making packaging, or else introduced into the actual entity, for example when it is made using a transparent substance such as glass, plastics, films, etc.

As already stated, this pellet is covered uniformly with the color corresponding to a determined wavelength, in other words a pentome.

The device according to the invention first of all aims to pick up the emission or absorption spectrum of this pentome, and to do this by means of an optical reader consisting, for example, of a pen. The latter is equipped with a waveguide, typically consisting of optical fibres, which makes it possible, on the one hand, to illuminate the identifier by channelling a polychromatic light beam from a source contained in said pen, typically of white light, and, on the other hand, to channel the waves reflected or transmitted by the identifier to a flat-field grating intended, as already explained, to diffract the waves reaching it into a plurality of monochromatic beams having a wavelength which is a function of the diffraction angle. This grating is integrated in the detection and identification device described previously in conjunction with FIG. 1.

Once the spectrum has been recognized, the microcomputer delivers a code or a unique reference corresponding strictly to the wavelengths of the color of the pellet. This code or this reference can be reconstructed in many ways, for example visually, graphically on a screen or simply in analog or digital form in order to be transmitted to other elements or devices which can carry out defined operations as soon as they receive this particular code. It is thereby seen that a unique code corresponds to a defined set of wavelengths. This method can therefore be applied to numerous uses in different fields, in particular direct measurement of the pH of a colored solution.

It may, in particular, be used in production lines in order to identify a series of colored objects without additional handling. In addition, it can be used for identifying or monitoring paints, pigments, and any colored liquids. By way of corollary to these two applications, this method can be applied to "color" vision of robots, which can thus obtain additional data regarding tests or decision making, thereby reducing human intervention.

It is therefore seen that the device of the invention makes it possible to provide an intelligent optical scanner insofar as it is capable of treating, on-line and instantaneously, the data output by a multiwave-length detector which picks up electromagnetic spectra emitted by any entities. It therefore constitutes the basis of an expert system which can be used in many fields.

We claim:

1. A compact portable device capable of operating in a hostile environment to carry out qualitative and quantitative identification of one or of a plurality of physicochemical entities contained in a sample capable of producing a spectra under excitation by electromagnetic waves that includes:

a portable compact casing that shields equipment housed therein from magnetic fields, electric fields, and external pressure variations;

a polychromator having an optical path within said casing to which emissions, absorption or reflective spectrum of a liquid, solid or gas sample are transmitted and analyzed, having said spectrum being decomposed into a sequence of signals having discrete variation in wavelength;

detecting means for detecting said discrete wavelength signals positioned on the optical path of the polychromator;

conversion circuit means coupled to said detecting means for converting said discrete wavelength signals into electrical signals; and, processing means having a plurality of standard spectra represented of known entities in memory for analyzing the spectra embodied in said electric signals and to decorrelate and compare the spectra with that stored in memory and to determine the nature and concentration in said sample.

2. The device of claim 1 wherein said conversion means is a charge coupled device (CCD).

3. The device of claim 1 further including an electrical supply generator having at least one photoelectric cell located outside of said casing.

* * * * *